(12) United States Patent
Juette et al.

(10) Patent No.: US 8,873,140 B2
(45) Date of Patent: Oct. 28, 2014

(54) ATR OBJECTIVE FOR AN IR MICROSCOPE AND METHOD FOR OPERATION THEREOF

(75) Inventors: Michael Juette, Karlsruhe (DE); Matthias Boese, Koenigsbach-Stein (DE); Rolf Steinbrunn, Leimersheim (DE)

(73) Assignee: Bruker Optik GmbH, Ettlingen (DE)

( * ) Notice: Subject to any disclaimer, the term of this patent is extended or adjusted under 35 U.S.C. 154(b) by 619 days.

(21) Appl. No.: 13/067,904

(22) Filed: Jul. 6, 2011

(65) Prior Publication Data

US 2012/0008196 A1    Jan. 12, 2012

(30) Foreign Application Priority Data

Jul. 9, 2010   (DE) .......................... 10 2010 031 189

(51) Int. Cl.

| | |
|---|---|
| *G02B 21/00* | (2006.01) |
| *G02B 21/24* | (2006.01) |
| *G02B 21/06* | (2006.01) |
| *G01N 21/55* | (2014.01) |
| *G02B 17/06* | (2006.01) |
| *G02B 7/182* | (2006.01) |

(52) U.S. Cl.
CPC ............ *G02B 21/0004* (2013.01); *G02B 21/24* (2013.01); *G02B 21/06* (2013.01); *G01N 21/552* (2013.01); *G02B 17/061* (2013.01); *G02B 7/1822* (2013.01)
USPC ............ 359/387; 359/350; 359/368; 359/385

(58) Field of Classification Search
CPC ........ G02B 7/00; G02B 7/1822; G02B 7/198; G02B 21/00; G02B 21/04; G02B 21/24; G01N 21/04; G01N 21/86; G01N 21/4738; G01J 3/453

USPC ................ 359/350, 351, 364–366, 368, 383, 359/391–392, 399, 405, 409, 896
See application file for complete search history.

(56) References Cited

U.S. PATENT DOCUMENTS

| | | | | |
|---|---|---|---|---|
| 4,134,638 | A | * | 1/1979 | Drauglis ....................... 359/364 |
| 4,833,348 | A | * | 5/1989 | Hannai ......................... 326/106 |
| 5,093,580 | A | * | 3/1992 | Sting ........................ 250/559.16 |
| 5,347,364 | A | * | 9/1994 | Kawasaki et al. ............. 356/445 |
| 5,581,085 | A | | 12/1996 | Reffner |
| 5,729,018 | A | * | 3/1998 | Wells et al. .............. 250/339.08 |
| 8,223,430 | B2 | * | 7/2012 | Hoult et al. ................... 359/391 |

FOREIGN PATENT DOCUMENTS

EP          0 730 145        4/2003

OTHER PUBLICATIONS

"Hyperion", user manual, Bruker Optik GmbH, Ettlingen / Germany 3 rd edition, May (2010).

* cited by examiner

*Primary Examiner* — Thong Nguyen
(74) *Attorney, Agent, or Firm* — Paul Vincent (57) ABSTRACT

An ATR objective (1) for an IR microscope has a Cassegrain objective (2), an ATR crystal (7), a holding bar (8) to one end of which on the side of the sample, the ATR crystal (7) is mounted, a holding element (10), thin struts (9) which rigidly connect the holding bar (8) to the holding element (10) and intersect an optical path of the ATR objective (1) entering or exiting the Cassegrain objective (2) in such a fashion that they shade less than 10% of the beam cross-section of the optical path, and a motor drive (12) for axial movement of the holding element (10) relative to the sample position (3). The automated ATR objective thereby enables simple adjustment of operating modes and different contact pressures of the ATR crystal with respect to a sample (19).

12 Claims, 5 Drawing Sheets

Fig. 3

ATR OBJECTIVE FOR AN IR MICROSCOPE AND METHOD FOR OPERATION THEREOF

This application claims Paris Convention priority from DE 10 2010 031 189.8 filed Jul. 9, 2010 the complete disclosure of which is hereby incorporated by reference.

BACKGROUND OF THE INVENTION

The invention concerns an ATR (attenuated total reflection) objective for an IR (infrared) microscope.

An IR microscope of this type comprising an ATR crystal is disclosed e.g. in U.S. Pat. No. 5,581,085.

Infrared (IR) spectroscopy is used to obtain analytical information about a sample. The chemical bonds in the sample absorb or reflect IR light in dependence on the wavelength of the IR light.

For samples with insufficient reflectivity and insufficient transparency, the IR spectroscopic investigation by means of attenuated total reflection (ATR) may sometimes also be in the form of an internal reflection. With attenuated total reflection, IR radiation is guided through a crystal with a high refractive index in the IR range (e.g. of germanium), which contacts the surface of the sample. The IR radiation marginally enters the sample, thereby producing sufficient interaction for a spectroscopic analysis, and is subsequently guided back through the crystal and detected by an IR detector. A good ATR measurement requires intimate contact between the ATR crystal and the sample, for which purpose the ATR crystal is pressed onto the sample, in most cases using a spring. Different contact pressures are used for different sample types (in particular sample hardnesses).

An IR microscope obtains analytical information specifically for a certain location or a certain area of the sample. An IR microscope advantageously has both an optical path for visible light and an optical path for IR light. Due to the largely common optical path of the visible light and the IR light, one can view with the visible light the location or area of the sample from which the analytical information is obtained by the IR light.

In an IR microscope with an ATR objective in the optical path, the ATR crystal fundamentally obstructs observation of the sample with visible light. For this reason, the ATR crystal must be removed from the optical path in the optical observation mode. Towards this end, the ATR crystal according to prior art is manually pivoted to the side or manually removed from the sample position in an upward direction. According to the "HYPERION Benutzerhandbuch" (HYPERION manual) of the company Bruker Optik GmbH, Ettlingen, Germany, pages 79 to 81 (2010), locking of an ATR crystal holder is released by means of a rocker switch and the holder is manually adjusted between an upper position for an optical observation mode and a lower position for an IR-ATR measuring mode. The holder is thereby moved below a Cassegrain objective. Several axial locking positions below the upper position allow adjustment of different pressure stages for contact with the sample.

Manual change of the operating modes and of the pressure stages is complex and limits the possibilities for automated sample investigations. There are no practicable automated ATR objectives to date.

It is the underlying purpose of the present invention to provide a practical automated ATR objective for an IR microscope, in particular, for facilitating changing of the operating modes and different contact pressures of the ATR crystal with respect to a sample.

SUMMARY OF THE INVENTION

This object is achieved by an ATR (attenuated total reflection) objective for an IR (infrared) microscope, comprising:
a Cassegrain objective which focuses on a sample position, the two mirrors of which each have a central bore,
an ATR crystal,
a holding bar which is guided through the two central bores and to one end of which on the side of the sample, the ATR crystal is mounted,
a holding element which is disposed in the area or beyond the side of the Cassegrain objective facing away from the sample,
thin struts which rigidly connect the holding bar to the holding element and intersect an optical path of the ATR objective entering or exiting the Cassegrain objective, in such a fashion that they shade less than 10% of the beam cross-section of the optical path, and
a motor drive for axial movement of the holding element relative to the sample position.

The present invention also concerns a method for operating an inventive ATR objective as described above, comprising lifting element, spring configuration and axial stop, comprising the following steps:
a) the holding element is moved to the sample position using the motor drive;
b) as soon as a measuring surface of the ATR crystal has exceeded the sample position by a predetermined axial distance S1, the axial movement of the holding element is stopped by the stop;
c) the lifting element is moved by the motor drive against the force of the spring configuration away from the sample position via a previously selected axial distance S2, thereby pressing the holding element or the holding bar against the stop;
d) a sample is axially moved from a side facing away from the Cassegrain objective to the sample position by means of a lifting table, is brought into contact with the ATR crystal and moved further until the measuring surface of the ATR crystal is in the focus of the Cassegrain objective. This method permits automated measurement of a sample on an inventive ATR objective. S1 determines the distance by which the sample must lift the ATR crystal in step d) and this distance is substantially determined by the objective geometry. S2 determines the contact force that the ATR crystal exerts on the sample. S2 thereby generally determines the spring strength in step c) (e.g. through contact with different spring elements with different paths of movement). The contact force according to step d) also results from path S1, for significant lengths S1 (in most cases, S1 influences the contact force only to a small degree due to the use of lifting elements). During step c), the lifting element moves relative to the frame structure ("lifting"). During step d), the holding element and the lifting element are mutually fixed via the motor drive such that the lifting element is lifted by the lifting table above the holding bar. This axial movement is opposed by the spring force of the spring configuration and/or weight force of the axially movable parts of the ATR objective. After step d), IR measurement on the sample can be carried out.

Advantages of the invention can be extracted from the description and the drawing. The features mentioned above and below may be used in accordance with the invention either individually or collectively in arbitrary combination. The embodiments shown and described are not to be understood as exhaustive enumeration but have exemplary character for describing the invention.

The invention is illustrated in the drawing and explained in more detail with reference to embodiments. In the drawing:

BRIEF DESCRIPTION OF THE DRAWING

FIG. 1b shows a schematic vertical cross-section of the ATR objective of FIG. 1a;

FIG. 2b shows a schematic vertical cross-section of the ATR objective of FIG. 2a;

FIG. 3 shows a schematic inclined view from below of the ATR objective of FIG. 2a;

FIG. 4 shows a schematic plan view of the ATR objective of FIG. 2a;

DESCRIPTION OF THE PREFERRED EMBODIMENT

The inventive ATR objective for an IR microscope has an opening in each of the two mirrors of the Cassegrain objective for guiding a holding bar for the ATR crystal through these openings. The holding bar is mounted to a holding element by means of thin struts beyond the Cassegrain objective (in the IR microscope above it) or also in the area of the bore of the Cassegrain mirror facing away from the sample. The thin struts intersect the optical path but hardly impair the optical observation function and IR measuring functions of the ATR objective due to their small surface. The holding element, which is disposed outside of the optical path and is axially guided, is hinged to a motor drive which is used to adjust, by means of a motor, the axial position of the holding element and therefore also of the ATR crystal.

The invention changes the mechanical access to the ATR crystal away from the area close to the sample to (in the IR microscope) above the Cassegrain objective to provide sufficient space for transmission and drive motor function. The space above the Cassegrain objective may thereby also be well utilized for motorized adjustment of the contact pressure on the sample. This greatly simplifies automation of the ATR objective.

The motor function for the axial drive of the ATR crystal and, if necessary, for adjustment of the contact pressure is preferably actuated via an electronic control device. The ATR objective may be supplemented by a lifting table for the sample, which can be actuated by a motor (typically in a vertical z direction) and is preferably also actuated via the electronic control device. The lifting table may also comprise motorized adjustment in the sample plane (typically the horizontal xy plane) for scanning the sample.

In one preferred embodiment of the inventive ATR objective, a first travel sensor is provided for detecting the axial position of the holding bar relative to the frame structure. The travel sensor can therefore be used to trace the position of the holding bar relative to the sample position or the focal plane of the Cassegrain objective, in particular, for adjusting the axial position of movement of a lifting table with the sample or for tracing or adjusting the contact pressure on the sample.

In one particularly preferred embodiment, a lifting element is disposed on a frame structure such that it can be axially moved, wherein the frame structure is rigidly connected to the Cassegrain objective, the holding element is coupled to the lifting element and, depending on the operating state, can be axially moved relative to the lifting element by means of the motor drive or is fixed, and a spring configuration is provided for providing a counterforce, in particular, an increasing force, to an axial movement of the lifting element away from the sample position. The motor drive may thereby move the holding element and the lifting element relative to each other in an axial direction or fix them with respect to one another. During fixing to the motor drive, a force is provided through the lifting element and the spring configuration. The force counteracts movement of the ATR crystal towards the Cassegrain objective (in an upward direction). It should be noted that this force may be based on spring action or even completely or partially on the weight force of the movable parts (mainly the lifting element). The strength of this force can advantageously be selected via the relative position of movement of holding element and lifting element, and therefore the contact pressure of the ATR crystal on the sample. The same motor drive can then adjust both the operating mode (optical observation or IR-ATR measurement) and also adjust the contact pressure during the IR-ATR operation. It should be noted that with suitable design of the motor drive and of the spring configuration, the contact force can be continuously adjusted.

In one advantageous further development of this embodiment, the spring configuration comprises several spring elements such that the spring constant of the overall spring configuration varies with the axial position of the lifting element, in particular, wherein the spring constant of the overall spring configuration increases with increasing axial separation between the lifting element and the sample position. This permits adjustment of a larger area of possible contact forces using little space. It is e.g. possible to use spring elements which are disposed in parallel and have a different basic length and contact both the lifting element and the frame structure only starting from a certain adjustment position.

In one advantageous further development, a relief spring is provided between the lifting element and the frame structure for complete or partial compensation of the dead weights of the axially movable parts. The relief spring (which may be one of several spring elements of the spring configuration) preferably substantially completely compensates for the dead weights of the axially movable parts. This also allows exertion of small contact pressures on the sample, since the dead weight of the movable parts need not be supported by the sample when the sample is contacted. Axially movable parts are, in particular, the holding bar, the holding element, and the lifting element (and any further components that are fastened to these parts).

In a preferred further development, one or several crank elements are provided for reducing the axial movement of the lifting element relative to the sample position with respect to the spring configuration. The crank element(s) constrain the full path of the lifting element relative to the sample position (or to the frame structure) such that only a fraction (typically between 1/3 and 1/20, often approximately 1/10) of this path acts with respect to the spring configuration. For this reason, the counterforce of the spring configuration can be kept approximately constant at least over the path of the lifting element upon contact between the ATR crystal and the sample (and generally also within one force stage), which facilitates adjustment of a defined contact force of the sample on the ATR crystal. In order to be able to adjust different contact force strengths (force stages), one can e.g. use a spring configuration comprising several parallel spring elements. When several spring elements are used, it is typical to use one crank element for each spring element, but it is also possible to connect all spring elements to the same spring element.

In an advantageous further development, a second travel sensor is provided for detecting the axial position of the lifting element relative to the frame structure. It is thereby possible to trace or adjust the counterforce of the lifting element (as a result e.g. of the spring configuration).

In one particularly preferred embodiment, an axial stop for the holding element or the holding bar is formed on the frame structure. When the stop blocks movement of the holding element or the holding bar, the element driving the holding element (in general the lifting element to which the motor drive is mounted) is moved by the motor drive relative to the frame structure. This may be utilized, in particular, for adjusting the contact force.

In another particularly preferred embodiment, the motor drive comprises a piezo translator system. The piezo translator system has proven itself in practice. In comparison with an electric motor, it avoids, in particular, strong mechanical oscillations.

Figure 1A:
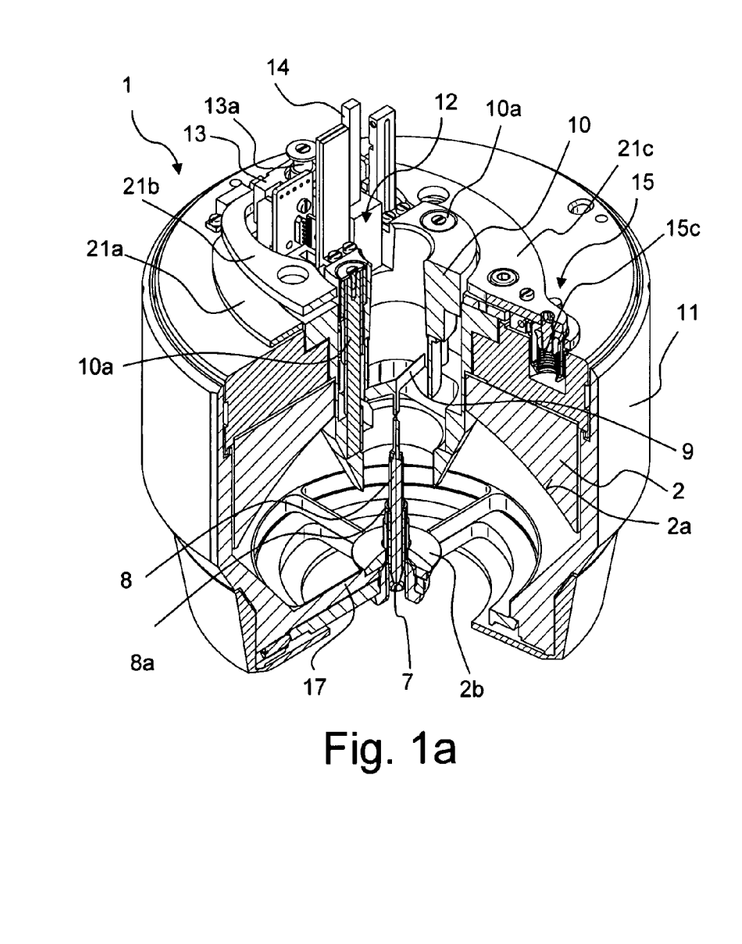
FIG. 1a shows a schematic cut-open inclined view of an inventive ATR objective in the optical observation mode.
Figure 1B:
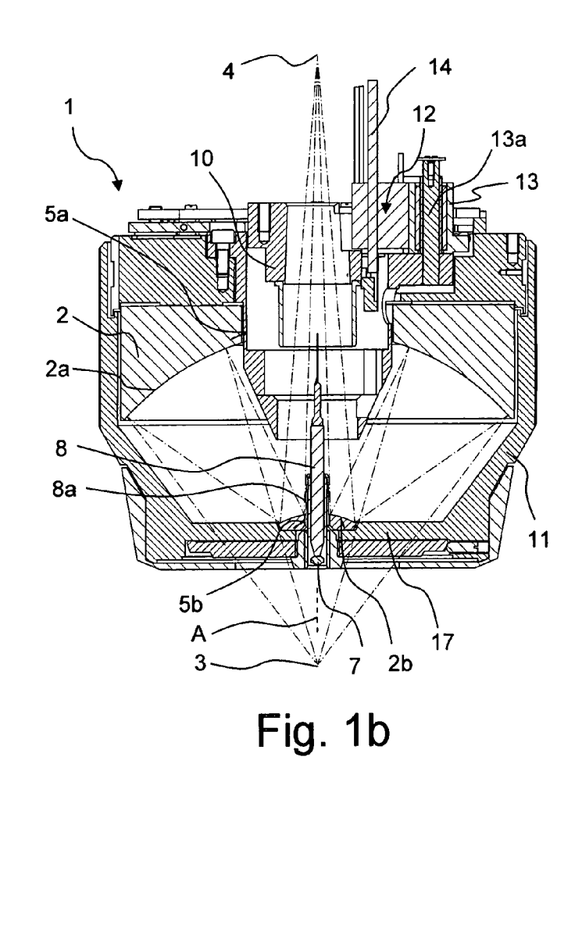

FIGS. 1a and 1b illustrate an inventive ATR objective 1 viewed from above at an inclined angle and in cross-section along an axis of symmetry A of a Cassegrain objective 2 which is integrated in the ATR objective 1.

In the illustrated optical observation mode, visible light emanating from a sample position 3 is reflected via a first concave mirror 2a of the Cassegrain objective 2 onto a second convex mirror 2b of the Cassegrain objective 2 and is reflected therefrom substantially parallel to the vertical axis A in an upward direction onto an intermediate focus 4. From the intermediate focus 4, the image of the sample (which is not illustrated) is e.g. imaged on a video camera (also not shown).

The two mirrors 2a, 2b have central bores (openings) 5a, 5b. These bores 5a, 5b, however, do not impair the imaging range, since the outer edge of the lower mirror 2b already similarly delimits the image. The bores 5a, 5b are used to hang an ATR crystal 7 in such a fashion that it can be moved.

Towards this end, the ATR crystal 7 is mounted to the lower end of a holding bar 8. The holding bar 8 is disposed in a vertical guide 8a. The upper end of the holding bar 8 is rigidly mounted to a holding element 10 via thin struts 9. The holding element 10 is disposed on bolt-like vertical guides 10a. The guides 8a, 10a are part of the (immovable) frame structure 11 of the ATR objective 1.

The holding element 10 is connected to a lifting element 13 via a motor drive 12. This lifting element 13 is, in turn, disposed on a bolt-like vertical guide 13a, which is also part of the frame structure 11. The holding element 10 forms a connecting linkage 14 in which the motor drive 12 engages. The motor drive 12 is disposed on the lifting element 13 such that, upon actuation of the motor drive 12, the holding element 10 can be axially moved towards the lifting element 13 and, upon locking of the motor drive 12, the lifting element 13 and the holding element 10 are mutually fixed. In the situation of FIGS. 1a, 1b, the holding element 10, and therefore the ATR crystal 7, are in an upwardly-moved position in which the ATR crystal 7 does not block the optical path for the visible light.

The lifting element 13 is coupled via an overall number of three crank elements 21a, 21b, 21c, which are disposed in the frame structure 11, to one of three respective spring elements. These three spring elements (of which only the third spring element 15c is shown in FIG. 1a), which together form a spring configuration 15, are also disposed in the frame structure 11. The lifting elements 21a-21c are used to translate the path of the lifting element 13 relative to the frame structure 11 into a (in the present case) 10 times smaller spring deflection. For this reason, the spring force changes only slightly during the stroke of the lifting element 13 (and, in particular, the path of movement of the sample in contact with the ATR crystal 7) such that well defined measuring ratios can be adjusted on the sample (with respect to the function of the spring elements 15a-15c, also see FIGS. 5a-5g).

Figure 2A:
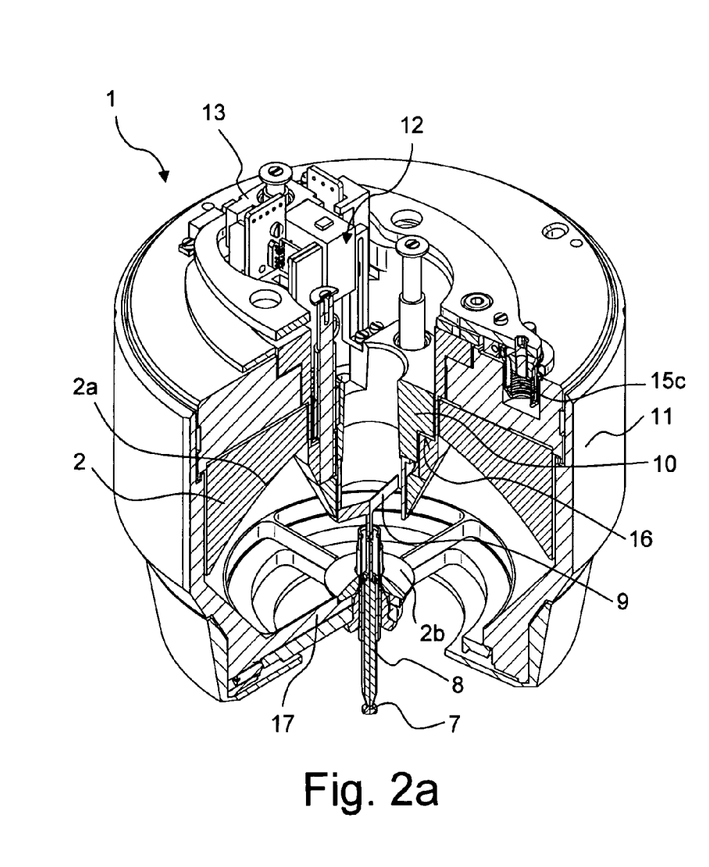
FIG. 2a shows a schematic cut-open inclined view of the ATR objective of FIG. 1a in the IR-ATR measuring mode.
Figure 2B:
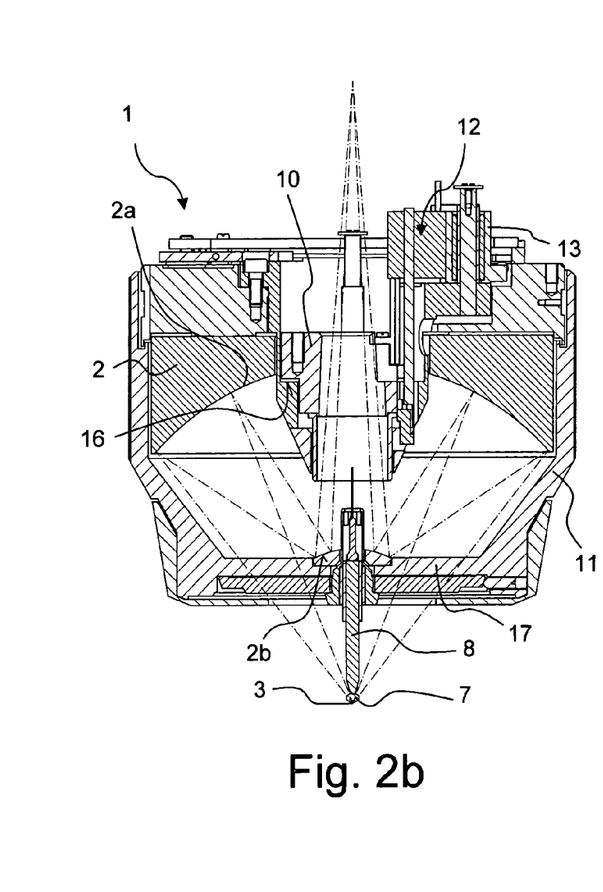

The holding element 10 may be moved downwards relative to the lifting element 13 by actuating the motor drive 12, which is formed as a piezo translator system in the present case. FIGS. 2a and 2b show a position in which the holding element 10 has been moved in a downward direction (into the upper Cassegrain mirror 2a facing away from the sample), which belongs to the IR-ATR measuring mode. The ATR crystal 7 is thereby in the optical path of the IR radiation which is guided through the ATR objective 1 similarly to the visible light in FIGS. 1a and 1b. A measuring surface on the lower side of the ATR crystal 7 is thereby at the sample position 3. The holding element 10 is supported on an axial stop 16 of the frame structure 11 such that, with further actuation of the motor drive 12, the lifting element 13 would move relative to the frame structure 11.

In both operating modes, the ATR crystal 7 is held in the axial center of the optical paths by means of the holding bar 8, and the holding element 10 surrounds the optical paths. The motor drive 12 and the lifting element 13 are disposed on the side of the optical paths and above the Cassegrain objective 2. For this reason, the optical paths are only minimally impaired (i.e. only by the thin struts 9) which generally causes much less shading than the holding struts 17 which hold the lower mirror 2b.

Figure 3:
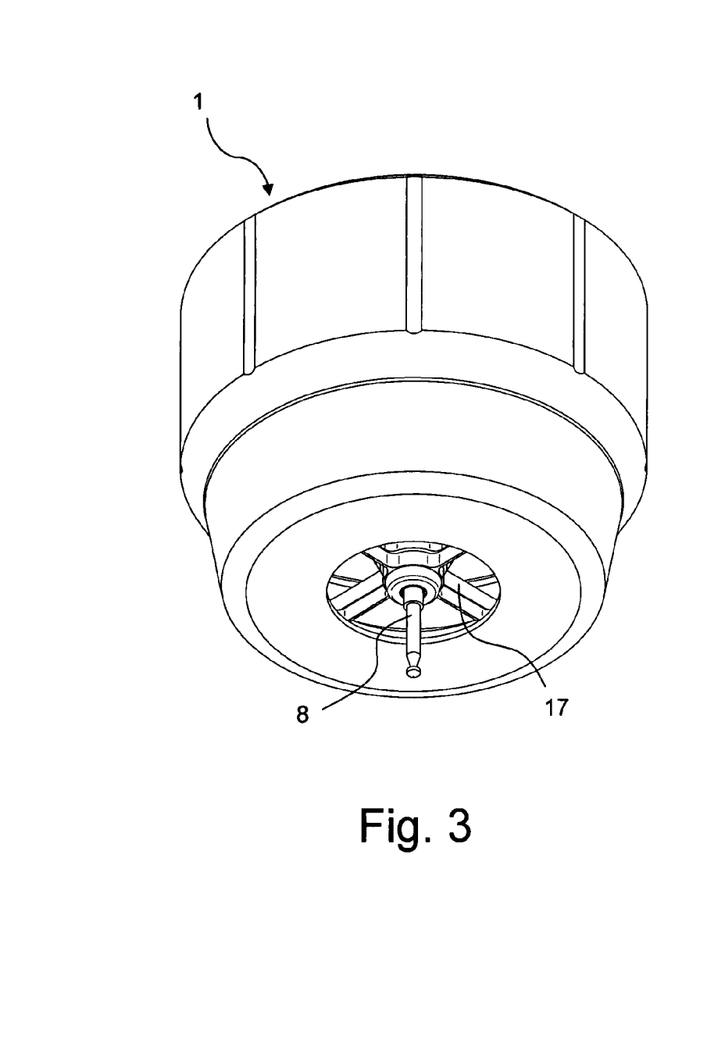
Figure 4:
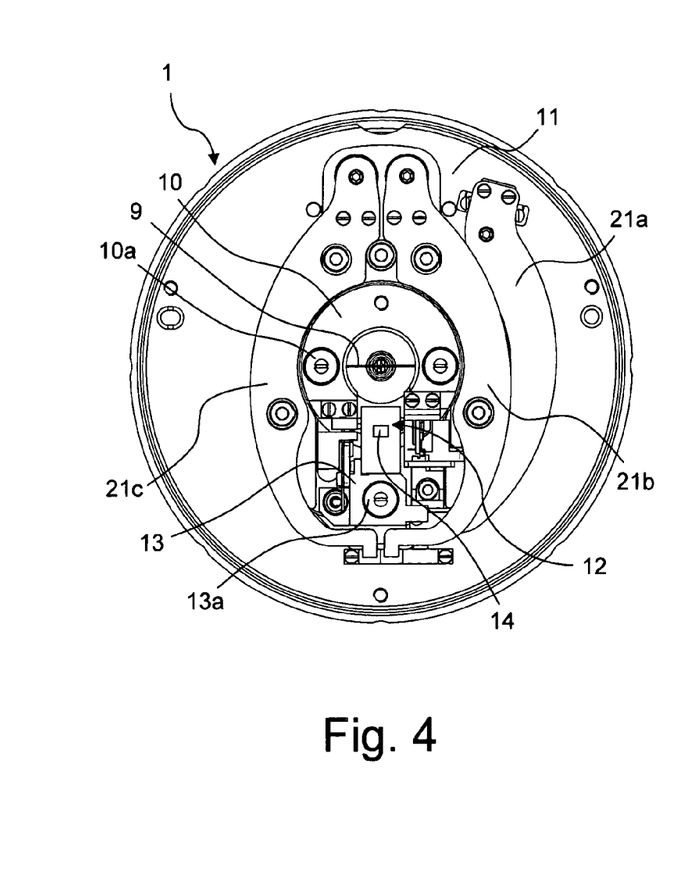

The holding struts 17 and also the thin struts 9 can be clearly seen in the inclined view from below of FIG. 3 and the plan view of FIG. 4. The thin struts 9 thereby occupy approximately 3% of the approximately circular cross-section of the optical path.

FIGS. 5a to 5g illustrate the use of an inventive ATR objective 1 (comparable to the ATR objective 1 of FIG. 1a) for preparing and performing an IR-ATR measurement, wherein the ATR objective 1 is illustrated in a highly simplified vertical cross-sectional view. In contrast to FIG. 1a, there is no translation of strokes and spring deflections with crank elements for better clarity.

Figure 5A:
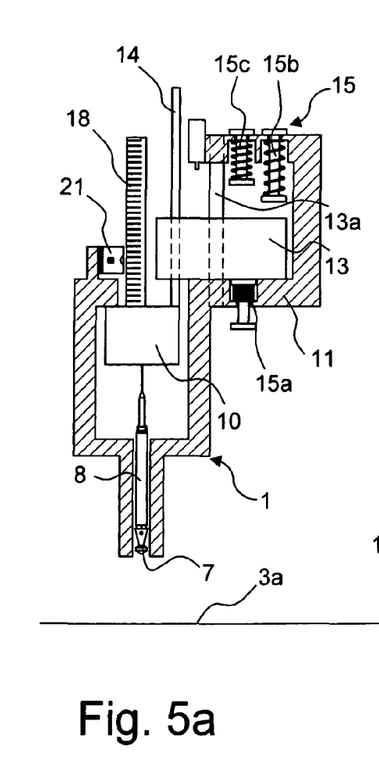
FIGS. 5a to 5g show schematic vertical cross-sectional views of an inventive ATR objective in different states of positioning of the ATR crystal.

FIG. 5a shows a parking position, wherein the ATR crystal 7 is withdrawn in an upward direction from the focal plane 3a which simultaneously defines the sample position in the axial (vertical) direction. In this position, a sample (not shown) can be optically observed. The ATR crystal 7 does not disturb observation.

The holding element 10 is pulled close to the lifting element 13 via the connecting linkage 14 by means of a motor drive which is not shown in detail. The lifting element 13 is disposed on a guide 13a which is securely formed in the frame structure 11. The frame structure 11 has a spring configuration 15, in the present case comprising three spring elements 15a, 15b, 15c for exerting force on the lifting element 13. In the position of FIG. 5a, the lifting element 13 is supported on the frame structure 11, wherein, however, the spring element 15a largely compensates for (cancels) the weight force of the axially movable parts, i.e. the lifting element (including the motor drive), the holding element 10 (including connecting linkage 14 and scaled measuring aid 18) and the holding bar 8 (including ATR crystal 7). The spring element 15a is therefore also referred to as a relief spring or compensation element.

The position of movement of the holding element 10 or the holding bar 8 can be followed via the scaled measuring aid 18 and/or a first electronic travel sensor 21.

Figure 5B:
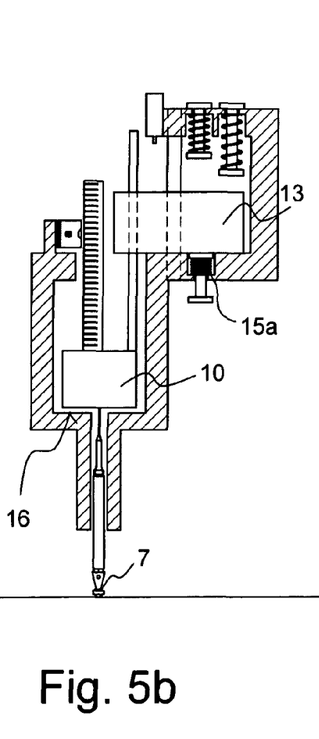

For preparing an IR-ATR measurement, the holding element 10 is moved away from the lifting element 13, i.e. in a downward direction, by means of the motor drive (not shown). FIG. 5*b* shows a position of movement in which the measuring surface (which has in most cases a size of only a fraction of a square millimeter) on the lower side of the ATR crystal 7 is just in the focal plane 3*a*. The holding element 10 has thereby not yet completely reached an axial stop 16. In this position, ATR reference measurement can be performed without contacting the sample.

Figure 5C:
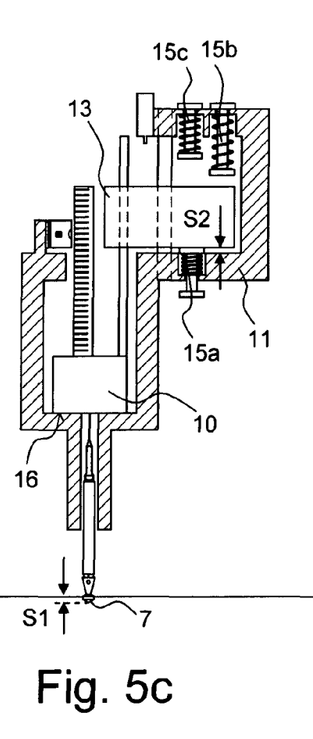

The holding element 10 is then slightly lowered by a further distance S1 until the holding element 10 has reached the stop 16 (cf. FIG. 5*c*). The further movement of the lifting element 13 away from the holding element 10 then "lifts" the lifting element 13 from the frame structure 11. FIG. 5*c* shows a position in which the lifting distance S2 is sufficiently small that the spring element 15*a* is indeed slightly relieved, but the upper spring elements 15*b*, 15*c* have not yet been contacted. The slight relief of the spring element 15*a* causes a reduction in the degree of compensation of the weight force of the movable parts (compared to FIG. 5*b*). A certain force (which corresponds to the non-compensated weight force of the movable parts, in the present case approximately 0.8N) is required for lifting the ATR crystal 7, i.e. with a sample that approaches from below. Extension of the distance S2 causes proportional increase of the force required for lifting the ATR crystal 7 (in as far as contact with the spring element 15*a* is not yet lost and the next spring element 15*b* has not yet been reached).

When S2 is increased to an intermediate position (which is performed by correspondingly driving the motor drive) (cf. FIG. 5*d*), the lifting element 13 of the illustrated example is finally released from the lower spring element 15*a*, upon which the full weight force of the movable parts is activated. The lifting element 13 additionally contacts the spring element 15*b*, which counteracts lifting of the ATR crystal (or of the movable parts). For lifting the ATR crystal 7, an average force (in the present case approximately 1.6N) is then required, wherein, by extending the distance S2, this force is proportionally increased (in as far as the further spring element 15*c* is not yet contacted).

Figure 5D:
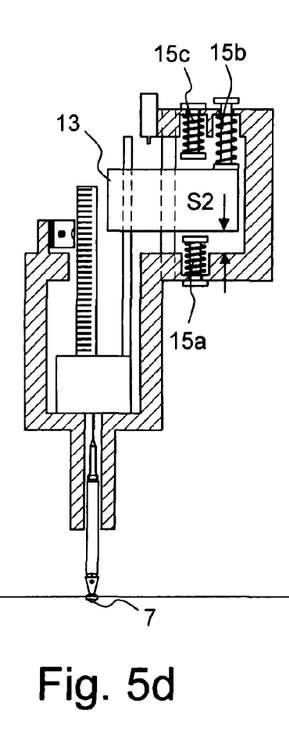
Figure 5E:
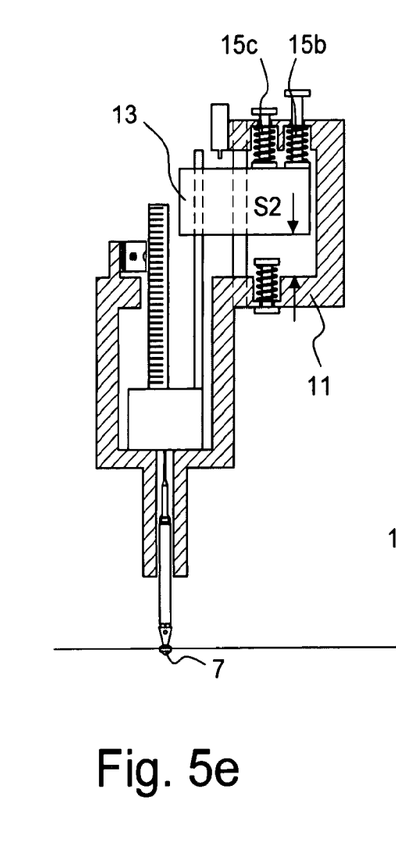

When S2 is further extended, the lifting element 13 contacts the further spring element 15*c* (cf. FIG. 5*e*). The force that is required for lifting the ATR crystal 7 thereby correspondingly increases (in the present case to approximately 3.2N). It is thereby also possible to further proportionally increase this force by further extending S2.

The counterforce for lifting the ATR crystal 7 can be continuously automatically adjusted via the motor drive (typically electrical) through S2 for all fields of application (of FIGS. 5*c*, 5*d* and 5*e*). If required, a second electronic travel sensor (not shown) can also follow the path of movement S2 between the lifting element 13 and the frame structure 11.

When the lifting element 13 has been moved by the desired distance S2, the sample 19 to be measured is moved from below to the ATR crystal 7 and the ATR crystal 7 is lifted together with the sample 19 until the measuring surface on the lower side of the ATR crystal 7 has returned to the focal plane 3*a* (cf. FIG. 5*f* relative to the initial position of FIG. 5*e*). A lifting table (not shown) on which the sample 19 is arranged can be used for this purpose. The holding element 10 is lifted from the stop 16 and the lifting element 13 is moved in an upward direction (in the present case against the force of the two spring elements 15*b*, 15*c*. It should be noted that in the present case the weight force of the movable parts must also be taken into consideration for lifting the ATR crystal 7.

Figure 5F:
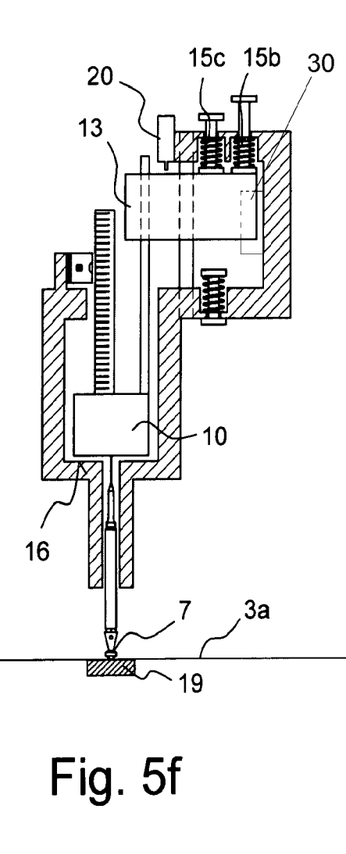

FIG. 5*f* also schematically illustrates a second travel sensor 30 for detecting an axial position of the lifting element 13 relative to the frame structure 11.

The force provided for lifting the ATR crystal 7 intensifies the contact between the measuring surface on the lower side of the ATR crystal 7 and the surface of the sample 19. It should be noted that the lifting path in FIG. 5*f* corresponds to the distance S1 of FIG. 5*c*. The actual ATR measurement (in most cases FTIR-ATR measurement) can then be performed on the sample 19.

Figure 5G:
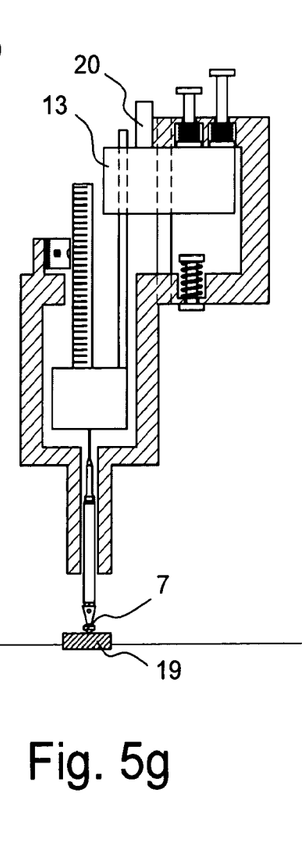

If the sample 19 or the ATR crystal 7 is lifted excessively high, the lifting element 13 moves towards a switch 20 via which an overload warning signal can be generated and/or a lifting table movement can be switched off (cf. FIG. 5*g*).

We claim:

1. An ATR (attenuated total reflection) objective for examination of a sample in an IR (infrared) microscope, the objective comprising:
    a frame structure;
    a Cassegrain objective cooperating with said frame structure, said Cassegrain objective focussing IR radiation onto the sample at a sample position, said Cassegrain objective comprising a first mirror having a first central bore and a second mirror having a second central bore;
    an ATR crystal;
    a holding bar guided through said first and said second central bores, said holding bar having an end facing the sample to which said ATR crystal is mounted;
    a holding element disposed proximate to or beyond a side of said Cassegrain objective facing away from the sample;
    thin struts, which rigidly connect said holding bar to said holding element and intersect an optical path of said ATR objective entering or exiting said Cassegrain objective, wherein said thin struts shade less than 10% of a beam cross-section of said optical path; and
    a motor drive for axial movement of said holding element relative to the sample position.

2. The ATR objective of claim 1, further comprising a first travel sensor for detecting an axial position of said holding bar relative to said frame structure.

3. The ATR objective of claim 1, further comprising a lifting element disposed on said frame structure for axial motion relative thereto, wherein said frame structure is rigidly connected to said Cassegrain objective and said holding element is coupled to said lifting element, wherein, in dependence on an operating state, said holding element is axially moved relative to said lifting element by means of said motor drive or is fixed relative to said lifting element and further comprising a spring configuration for providing a counterforce in response to axial movement of said lifting element away from the sample position.

4. The ATR objective in claim 3, wherein said counterforce is an increasing force.

5. The ATR objective of claim 3, wherein said spring configuration comprises several spring elements and a spring constant of an overall spring configuration varies with an axial position of said lifting element.

6. The ATR objective of claim 5, wherein said spring constant of said overall spring configuration increases with increasing axial separation between said lifting element and the sample position.

7. The ATR objective of claim 3, wherein a relief spring is disposed between said lifting element and said frame structure for complete or partial compensation of dead weight of axially movable parts.

8. The ATR objective of claim 3, wherein said lifting element comprises one or more lifting element components for reducing axial movement of said lifting element relative to the sample position with respect to said spring configuration.

9. The ATR objective of claim 3, further comprising a second travel sensor for detecting an axial position of said lifting element relative to said frame structure.

10. The ATR objective of claim 3, wherein said frame structure comprises an axial stop for said holding element or said holding bar.

11. A method for operating the ATR objective of claim 10, the method comprising the steps of:
   a) moving the holding element to the sample position using the motor drive;
   b) stopping axial movement of the holding element using the axial stop as soon as a measuring surface of the ATR crystal has exceeded the sample position by a predetermined axial distance (S1);
   c) moving the lifting element, using the motor drive, against a force of the spring configuration away from the sample position via a previously selected axial distance (S2), thereby pressing the holding element or the holding bar against the stop;
   d) axially moving the sample from a side facing away from the Cassegrain objective to the sample position to bring the sample into contact with the ATR crystal and further moving the sample until a measuring surface of the ATR crystal is in a focus of the Cassegrain objective.

12. The ATR objective of claim 1, wherein said motor drive comprises a piezo translator system.

\* \* \* \* \*